US009010186B2

(12) United States Patent  (10) Patent No.: US 9,010,186 B2
Pagano  (45) Date of Patent: Apr. 21, 2015

(54) METHOD AND APPARATUS FOR DETECTING INTERNAL RAIL DEFECTS

(75) Inventor: Dominick A. Pagano, Weston, CT (US)

(73) Assignee: Nordco Rail Services & Inspection Technologies, Inc., Beacon Falls, CT (US)

(*) Notice: Subject to any disclaimer, the term of this patent is extended or adjusted under 35 U.S.C. 154(b) by 192 days.

(21) Appl. No.: 13/462,971

(22) Filed: May 3, 2012

(65) Prior Publication Data

US 2013/0111997 A1 May 9, 2013

Related U.S. Application Data

(63) Continuation-in-part of application No. 12/108,401, filed on Apr. 23, 2008, now abandoned.

(51) Int. Cl.
G01N 29/04 (2006.01)
G01N 29/22 (2006.01)
G01N 29/265 (2006.01)
G01N 29/24 (2006.01)

(52) U.S. Cl.
CPC ............. G01N 29/04 (2013.01); G01N 29/225 (2013.01); G01N 29/265 (2013.01); G01N 2291/2623 (2013.01); G01N 29/043 (2013.01); G01N 29/221 (2013.01); G01N 29/2493 (2013.01); G01N 2291/056 (2013.01)

(58) Field of Classification Search
USPC .................................................. 73/635, 636
See application file for complete search history.

(56) References Cited

U.S. PATENT DOCUMENTS

| | | | |
|---|---|---|---|
| 3,415,110 A | 12/1968 | Cowan | |
| 4,044,594 A * | 8/1977 | Owens et al. | 73/621 |
| 4,165,648 A | 8/1979 | Pagano | |
| 4,174,636 A | 11/1979 | Pagano | |
| 5,339,692 A | 8/1994 | Shoenhair et al. | |
| 5,341,683 A * | 8/1994 | Searle | 73/597 |
| 5,386,727 A | 2/1995 | Searle | |
| 5,578,758 A | 11/1996 | Havira et al. | |
| 5,777,891 A | 7/1998 | Pagano | |
| 6,055,862 A | 5/2000 | Martens | |
| 6,516,668 B2 * | 2/2003 | Havira et al. | 73/636 |
| 6,604,421 B1 | 8/2003 | Li | |
| 7,213,459 B2 | 5/2007 | Sengupta | |
| 7,305,885 B2 * | 12/2007 | Barshinger et al. | 73/602 |
| 7,849,748 B2 * | 12/2010 | Havira | 73/639 |
| 7,882,742 B1 * | 2/2011 | Martens | 73/636 |
| 8,418,563 B2 * | 4/2013 | Wigh et al. | 73/649 |
| 8,424,387 B2 * | 4/2013 | Wigh et al. | 73/649 |
| 8,485,035 B2 * | 7/2013 | Wigh et al. | 73/636 |
| 2001/0032513 A1 | 10/2001 | Havira et al. | |
| 2008/0223137 A1 | 9/2008 | Bestebreurtje | |

FOREIGN PATENT DOCUMENTS

JP 2001305111 A 10/2001

* cited by examiner

Primary Examiner — J M Saint Surin
(74) Attorney, Agent, or Firm — Greer, Burns & Crain, Ltd.

(57) ABSTRACT

An ultrasonic rail inspection system designed to detect defects in a rail which result from longitudinal cracks that propagate in the horizontal and transverse plane of the rail. Detection of this type of defect is possible by directing an ultrasonic beam into the rail at a predetermined angle from the perpendicular to the surface of the rail. The predetermined angle must be sufficient to detect these normally undetectable defects and can be in the range of 8° to 14° from the perpendicular.

8 Claims, 12 Drawing Sheets

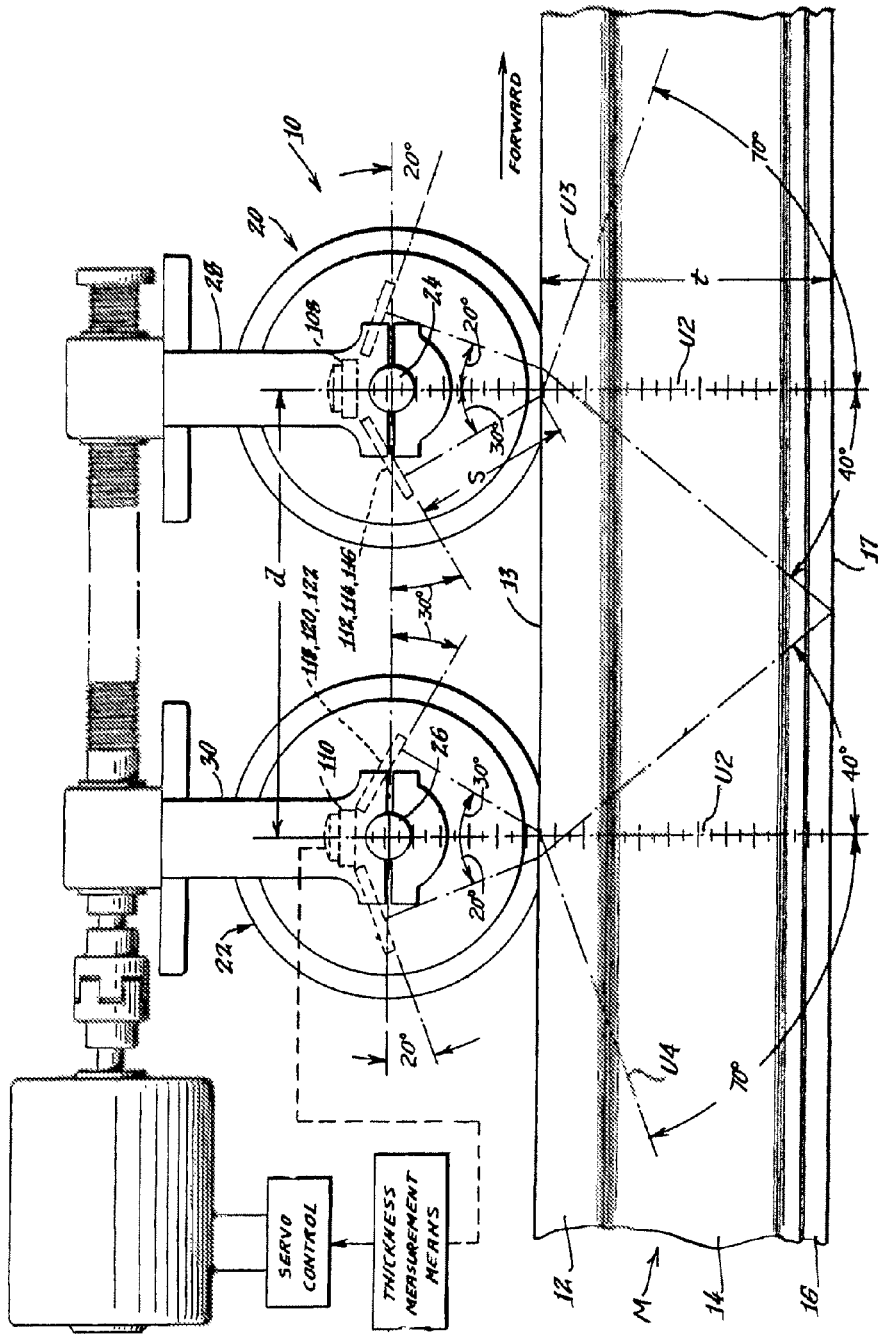

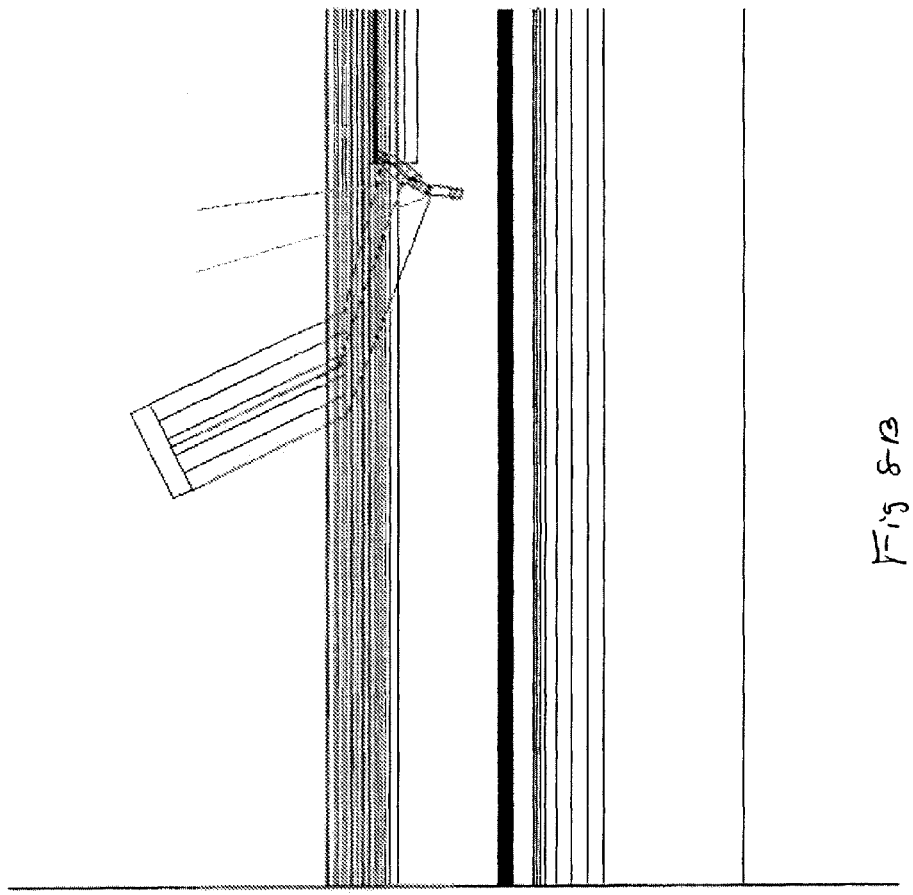
Fig 8-B
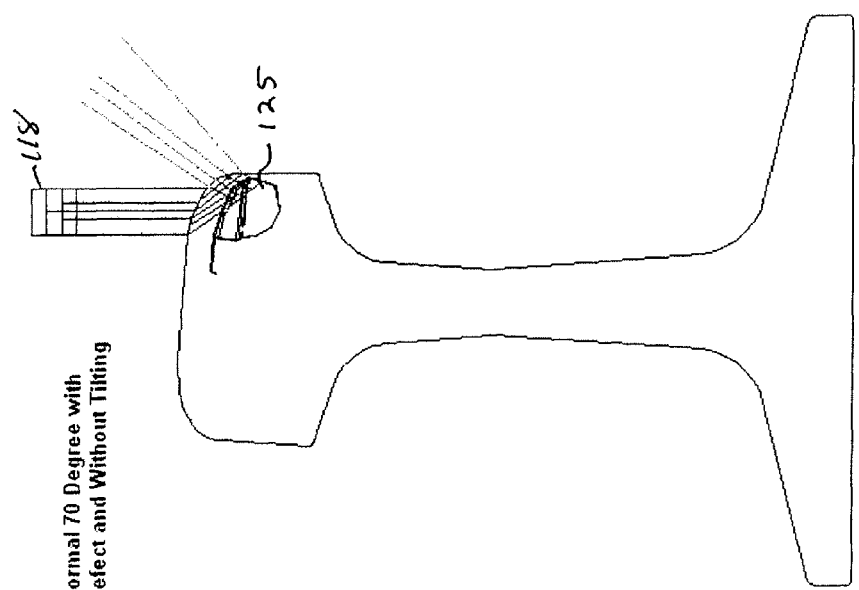
Normal 70 Degree with
Defect and Without Tilting
Fig 8-A 70 Degree Tilted 10 degrees 70 Degree Tilted 10 Degrees with defect

METHOD AND APPARATUS FOR DETECTING INTERNAL RAIL DEFECTS

CROSS-REFERENCE TO RELATED APPLICATIONS

This application is a continuation in part of U.S. patent application Ser. No. 12/108,401 filed Apr. 23, 2008, in the name of Dominick A. Pagano, and entitled Method And Apparatus For Detecting Internal Rail Defects. U.S. patent application Ser. No. 12/108,401 is hereby incorporated by reference in its entirety. This application also incorporates by reference U.S. Pat. No. 4,165,648 issued to inventor Dominick A. Pagano.

FIELD OF INVENTION

This invention relates to a method and apparatus for the ultrasonic inspection of a test material and more particularly to the ultrasonic inspection of a railroad rail which may contain detail fractures caused by metal fatigue.

BACKGROUND OF THE INVENTION

The Federal Railroad Administration (FRA) reported, as of Dec. 1, 2006, that between 1995 and 2005 a total of 276 derailments occurred on the four Class I U.S. railroads and that these derailments were caused by broken rails. One of these derailments occurred on Mar. 17, 2001 and involved the Amtrak California Zephyr bound from Chicago to Oakland, Calif. This derailment caused one fatality, 77 injuries and $338 million dollars in property damage. The cause was a broken rail later found to have multiple internal defects due to metal fatigue.

A study of service failures on Class I railroads by the Transportation Technology Center, Inc. (TTCI) indicates that certain internal rail defects may be undetectable with current ultrasonic technology. In particular, one of the more problematic defects to locate with existing technology are detail fractures that are caused by metal fatigue and are masked by rail surface and subsurface shelling conditions, rail head profile (i.e. heavily worn rail), orientation of the defect and transducer-to-rail coupling. The need exists to develop a detection technique that is capable of locating internal defects in railroad rails due to metal fatigue that have heretofore been difficult or impossible to detect.

It is an object of the present invention to provide more effective and complementary non-destructive testing (NDT) technologies to reliably detect internal rail defects even with rail surface damage, heavily worn railroad profiles and different transducer orientations.

U.S. Pat. Nos. 4,165,648 and 4,174,636, both of which are incorporated herein by reference, describe one prior art method for detecting fractures in a railroad rail. More particularly, these two patents describe a system and method for performing ultrasonic inspection of a length of test material, such as a rail, with an ultrasonic transducing system emitting a beam of ultrasonic energy from within a pair of leading and trailing sealed wheels transparent to the ultrasonic beam and arranged for rolling contact along the test material.

In each of the leading and trailing wheels, ultrasonic transducers are oriented so that a beam of ultrasonic energy emitted from a transducer in one wheel will enter the test material, be reflected from the bottom surface thereof, and be directed to and received by a transducer in the same wheel or the other wheel. A reading of the transmitted energy indicates whether energy has been deflected away from the receiving transducer by defects in the test material. The transducers in each wheel are arranged to alternately transmit and receive.

The leading and trailing wheels are also provided with a longitudinally-looking transducer for emitting a beam of ultrasonic energy into the test material in advance of and behind the moving wheel means, e.g., at an angle of about 70° perpendicular to the test material surface. Additional zero degree transducers in each wheel can also emit radiation perpendicular to the test material.

Although the teachings in these two prior art patents did improve upon the detection of fractures in a railroad rail certain detail fracture types remain difficult to detect. It is therefore an object of the present invention to provide a system and method for detecting detailed fractures in a test material, such as a railroad rail, that were heretofore difficult if not impossible to detect with known prior art technology.

Due to the high cost of railroad derailments, both in terms of property damage and human injury or death, various scientific and technical bodies have investigated the cause of internal rail defects to determine the specific characteristics of such defects that could be used to improve detection. Although various characteristics have been found which lead to rail failure those characteristics have not been detectable on a commercial scale as they are below the detectable threshold of ultrasonic technology currently used in the detection industry.

It is therefore another object of the present invention to provide a commercially viable detection system able to detect the heretofore undetectable characteristics of a railroad rail which can lead to rail failure.

SUMMARY OF THE INVENTION

The present invention is directed to a system for performing ultrasonic inspection of a rail and detecting detailed fractures which result from longitudinal cracks that propagate in the horizontal and transverse plane of the rail. Such defects are normally difficult or impossible to detect with ultrasonic beams directed perpendicular to the surface of the rail. The present invention advantageously directs the ultrasonic beam at an angle from the perpendicular to the surface of the rail sufficient to detect such cracks.

It is a feature of the invention that the beam is tilted from the perpendicular in an amount sufficient to detect detailed fractures which result from longitudinal cracks that propagate in the horizontal plane of the rail.

It is a further feature of the invention that the amount of tilt is in the range from about 8° to about 14° from the perpendicular.

Other objects and features of the invention will be apparent from the detailed description set forth herein considered together with the following drawings.

BRIEF DESCRIPTION OF THE SEVERAL VIEWS OF THE DRAWINGS

In the drawings:

1.
FIG. 1A illustrates a prior art ultrasonic rail detection system;
2.
FIGS. 6-10B illustrate use of the inventive system for detecting detail fractures.

DETAILED DESCRIPTION OF THE INVENTION

Figure 1B:
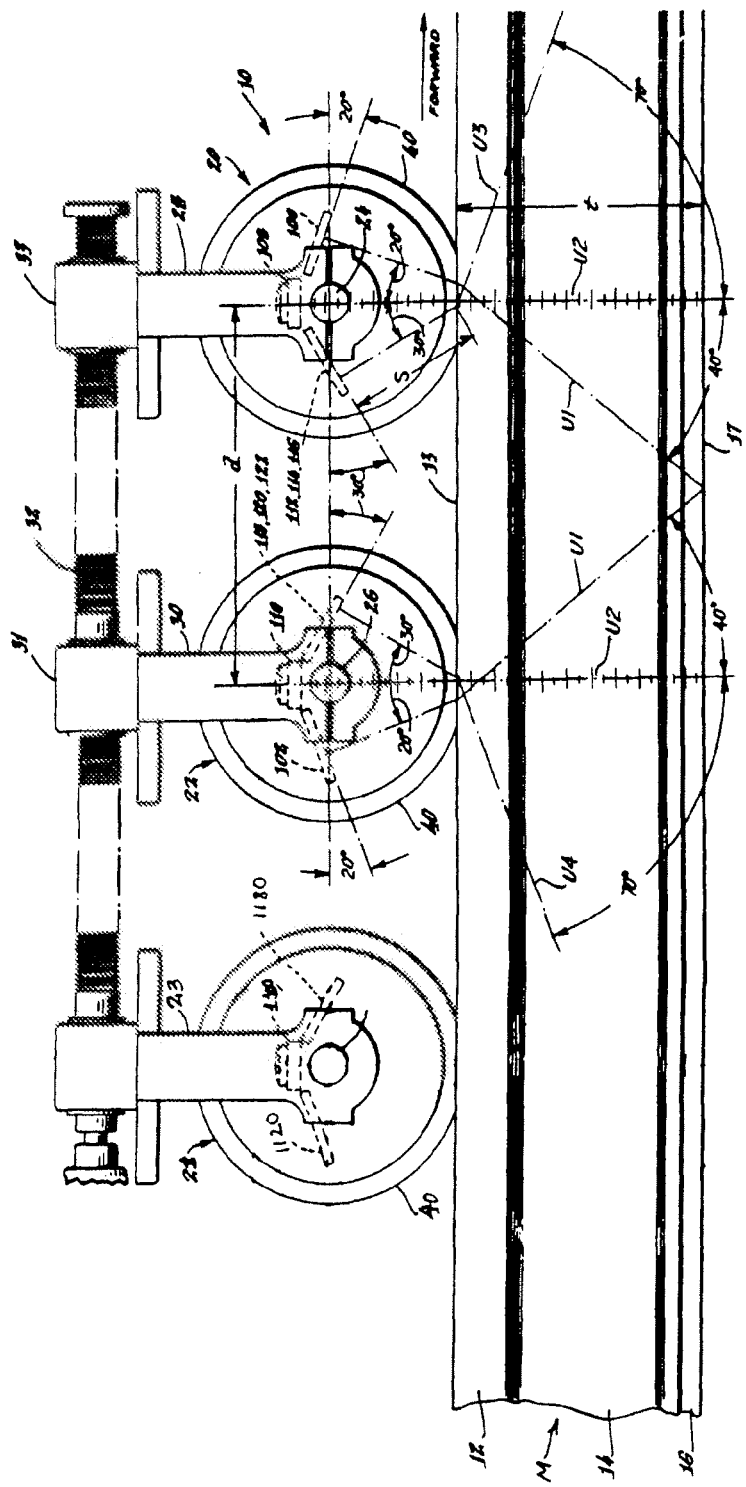
FIG. 1B illustrates a ultrasonic rail detection system according to the present invention;
3.

FIG. 1 illustrates a prior art two wheel ultrasonic inspection system 10 described in U.S. Pat. No. 4,165,648, which is arranged to detect flaws and defects in a length of test material M, illustrated as a rail having a substantially rectangular head 12 with an upper surface 13, a vertical web 14, and a base 16 with a bottom surface 17 typically resting on ties (not shown.)

Arranged for rolling contact along the upper surface 13 of rail head 12 are a leading test wheel 20 and a trailing test wheel 22. The wheels 20 and 22 rotate about fixed shafts 24 and 26 secured respectively to support arms 28 and 30 which are spring loaded downward by conventional means upon a carriage (not shown) which propels the wheels along the length of test material M.

As illustrated in FIG. 1 the leading and trailing wheels 20 and 22 have zero degree transducers 108 and 110 which are oriented to emit beams U2 of ultrasonic energy downward perpendicularly through Teflon (polyetrafluoroethylene) waveguides to surface 13 into the test material. The downward-looking (zero degree) transducers 108 and 110, used in a pulse echo mode, can indicate whether there is a head and web separation, and can indicate the presence of bolt holes, bolt hole cracks, and some vertical split heads that occur in the web region. These zero degree transducers can also detect the horizontal component of detail fractures as described below. It is to be noted that these zero degree transducers 108 and 110 are mounted high up within the wheel. This location advantageously provides a long travel path of at least two inches within the wheel, which avoids problems of undesired echoes interfering with the reflected energy U2 returning from the bottom 17 of the test material M. The Teflon waveguides serve to reduce beam divergence and thus also eliminate false echoes.

The leading wheel 20 further carries an array of three horizontally spaced transducers 112, 114 and 116 oriented to send a beam of ultrasonic energy U3 forwardly into the length of test material M and substantially longitudinally therein, e.g. at a resultant angle of 70° in steel, from a 60% water—40% glycol mixture, the transducers 112, 114 and 116 are oriented to emit a beam at an angle of about 28° to 30° to the perpendicular. In a similar manner, trailing wheel 22 is provided with a horizontally spaced array of three transducers 118, 120 and 122 oriented to send a beam U4 of ultrasonic energy in a rearward direction at a resultant angle of about 70° to the perpendicular. For purposes of the invention described herein a single wheel can be used to provide one or more of both zero degree transducer and 70 degree transducers.

Figure 2:
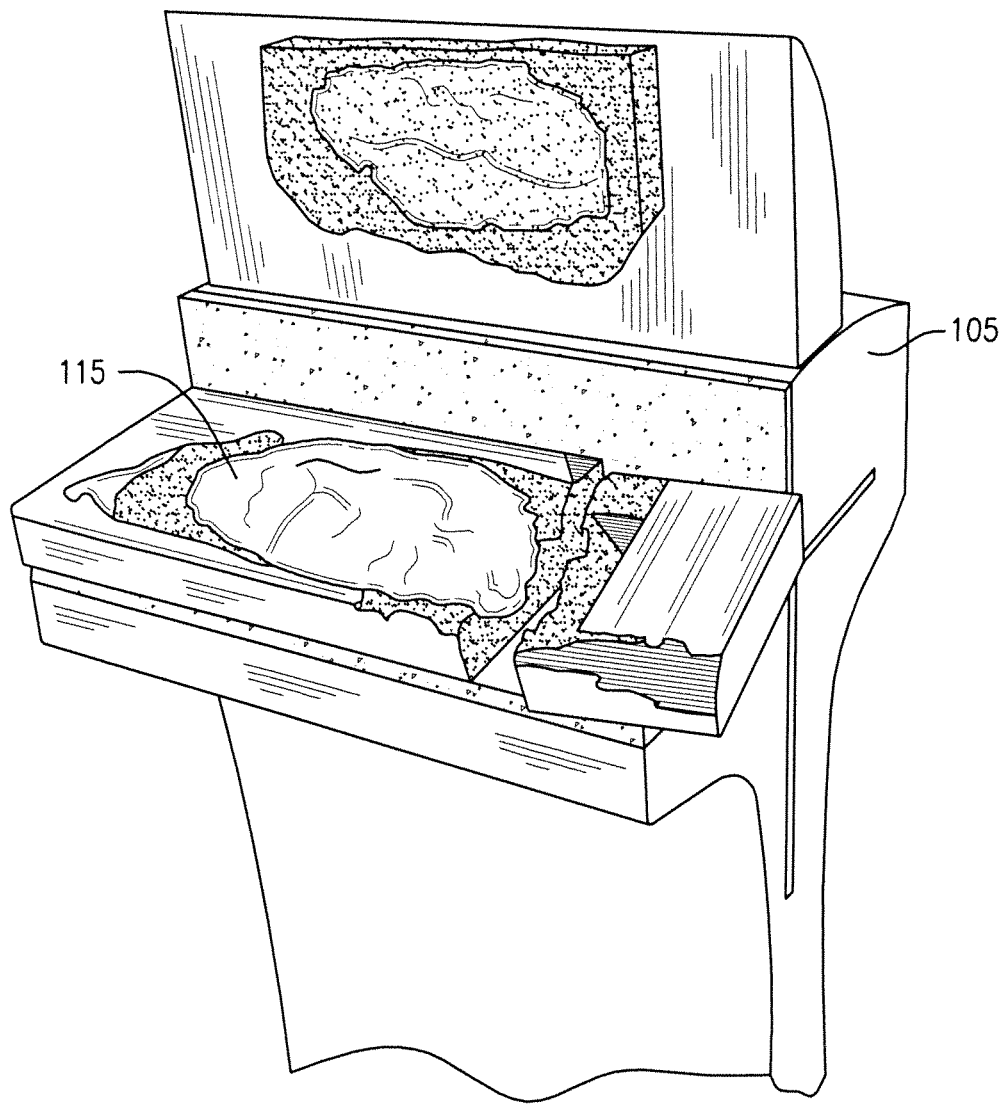
FIGS. 2-5 illustrate detailed fractures which can be detected with the invention; and 5.

Referring now to FIG. 2, there is shown a portion 105 of a railroad rail which has been cut into sections to reveal the existence of internal defect 115. Based on the analysis of samples such as rail portion 105 it has been determined that the genesis of this class of internal defects, such as defect 115 defined herein as a detail fracture, is that the defect starts out as a longitudinal seam that propagates in the horizontal plane to become a deep shell or horizontal split head as illustrated in FIG. 2.

Figure 3:
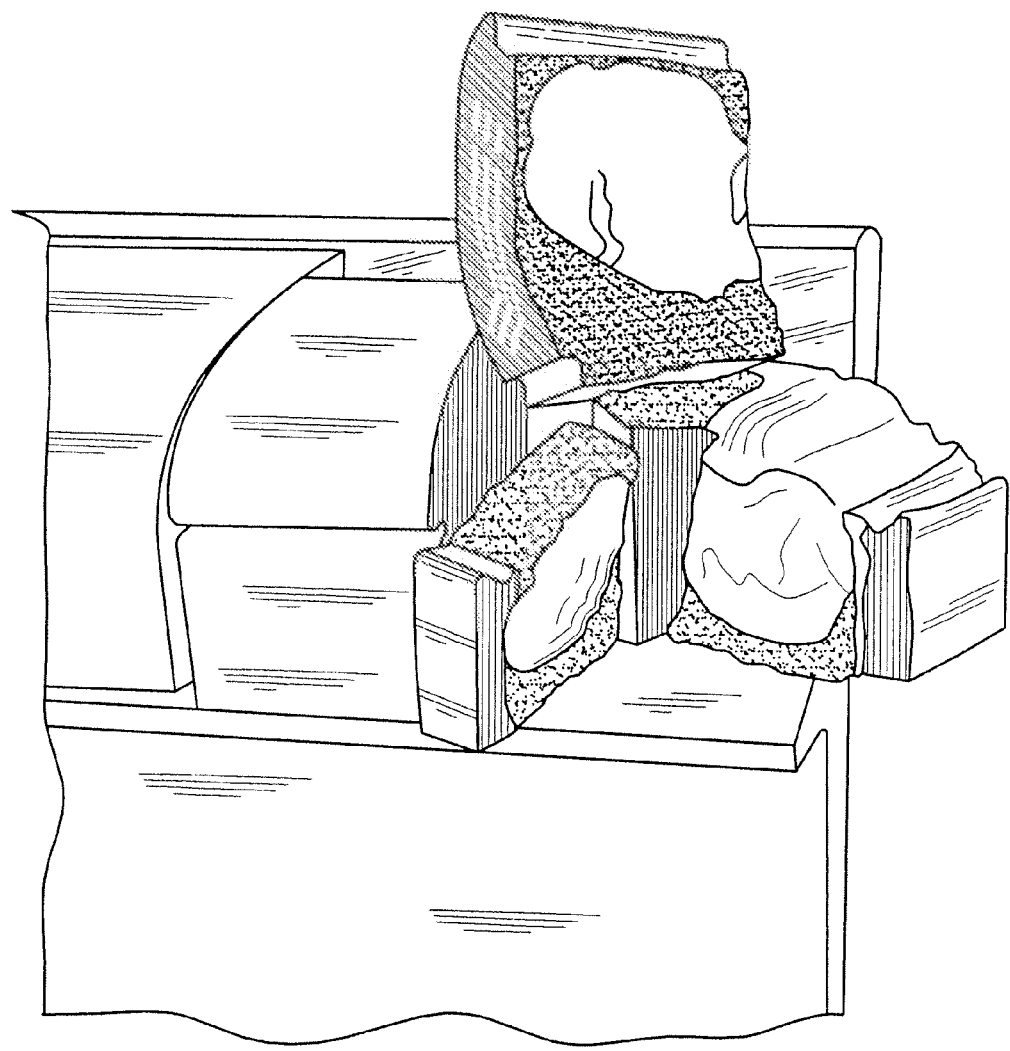
Figure 4:
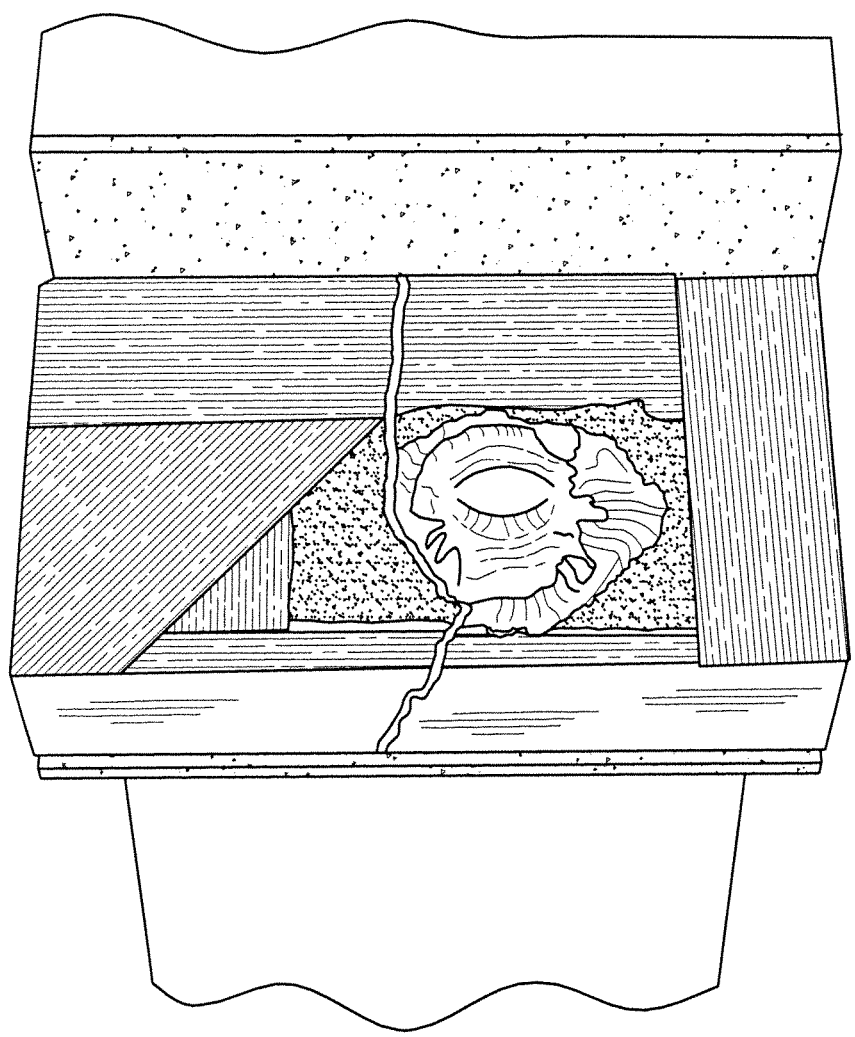
Figure 5:
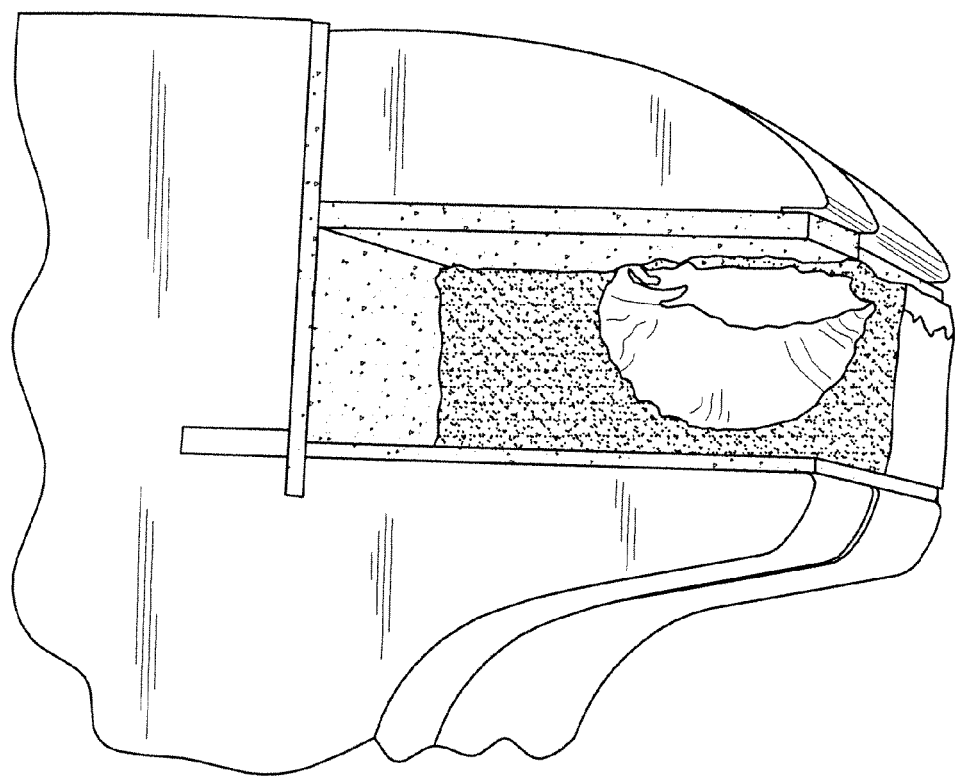

As a detail fracture, such as defect 115, continues to propagate its boundary can break to the outside surface. Also, as shown in FIG. 3 the horizontal growth of the defect will also propagate in a transverse direction. Current ultrasonic technology is not capable of detecting the horizontal components of these deep shells because they occur away from the centerline of the rail. Further, the difficulty in detecting the transverse components by the use of conventional ultrasonics is limited by the geometry of the rail head, in particular due to the outer edges where the surface condition can further cause excessive false alarms or "no test" conditions. Another feature that has been observed is that these types of detail fractures tend to run parallel to the surface and subsequently, unless a longitudinal transducer is oriented perpendicular to the surface, detection can be problematic. FIGS. 4 and 5 illustrate further examples of detail fractures showing both the horizontal component and the transverse component of the fracture.

Figure 1C:
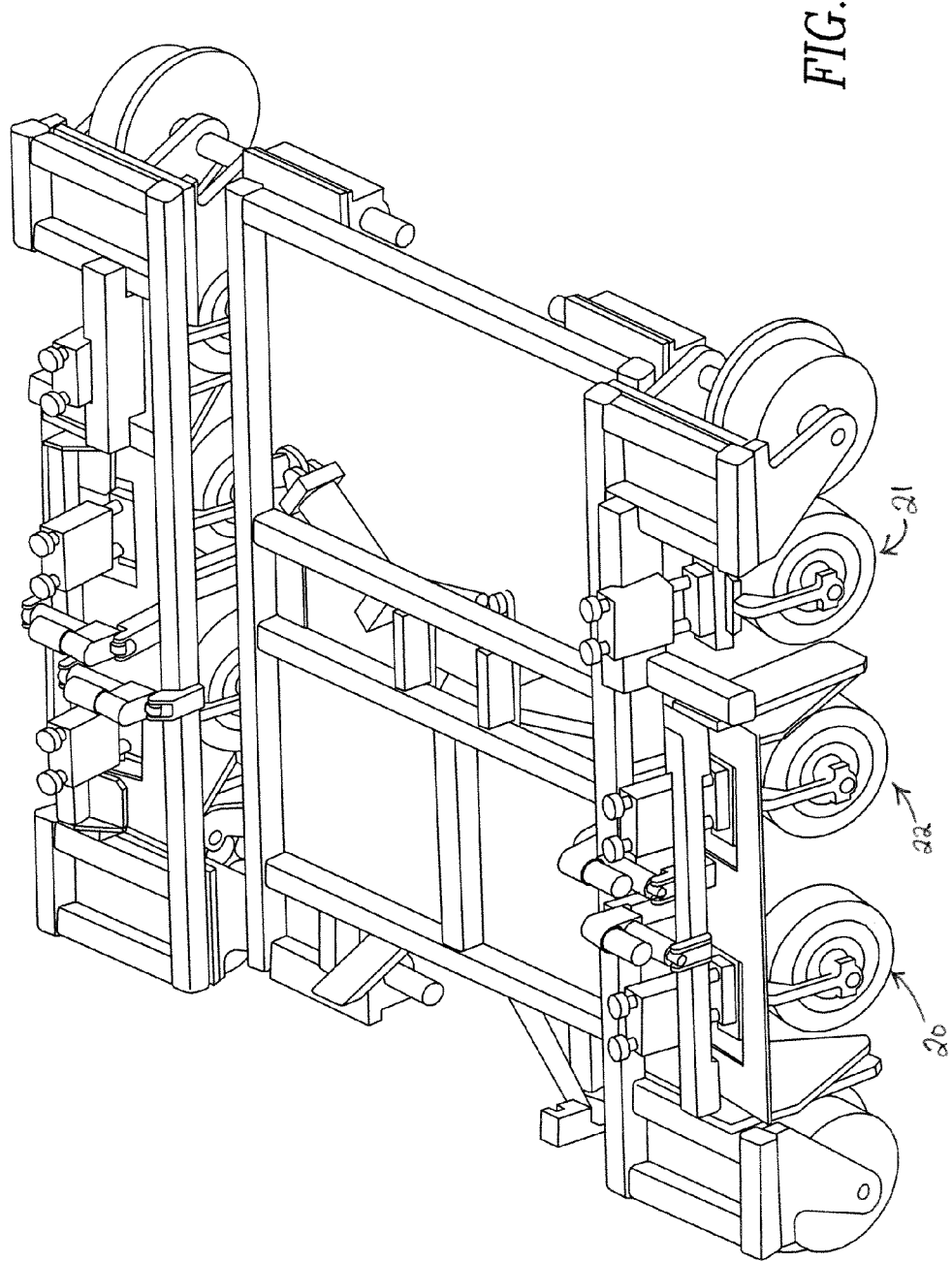
FIG. 1C illustrates a perspective view of the ultrasonic rail detection system according to the present invention;
4.

The prior art system shown in FIG. 1A shows the use of both a leading 20 and trailing 22 wheel. For purposes of the present invention a third single wheel 21 is shown in FIG. 1B and FIG. 1C and is used with the leading 20 and trailing 22 wheel. In one embodiment, the single wheel 21 has one zero degree transducer 1100 and two 70 degree transducers 1180, 1120. In other embodiments the single wheel 21 will have one or more than two of each zero degree transducer 1100 and 70 degree transducers. Operation of the zero degree transducer 1100 and the 70 degree transducers 1180, 1120 in the third wheel 21 will be in accordance with the teachings in U.S. Pat. No. 4,165,648.

The invention described herein deals with the utilization of a wheel probe 21 with multiple transducers as described above. However, this invention provides the means for the transducers to be angled in such a way as to have the transducer essentially perpendicular to the horizontal component of the detail fracture. In one embodiment, arm 23 mounts the wheel 21 at a fixed angle with respect to a vertical plane extending perpendicular from the top of the rail without any adjustment to the angle or the lateral location of the wheel 21. This allows the detection of the horizontal defects with the zero degree transducer 1100 and the detection of transverse components of the defects utilizing the forward and aft looking 70 degree transducers 1120, 1180. This feature therefore uses both the horizontal and transverse signs of such defects and renders a more robust system, minimizing false alarms due to anomalies such as head checking, surface engine burns and other surface conditions.

Figure 6:
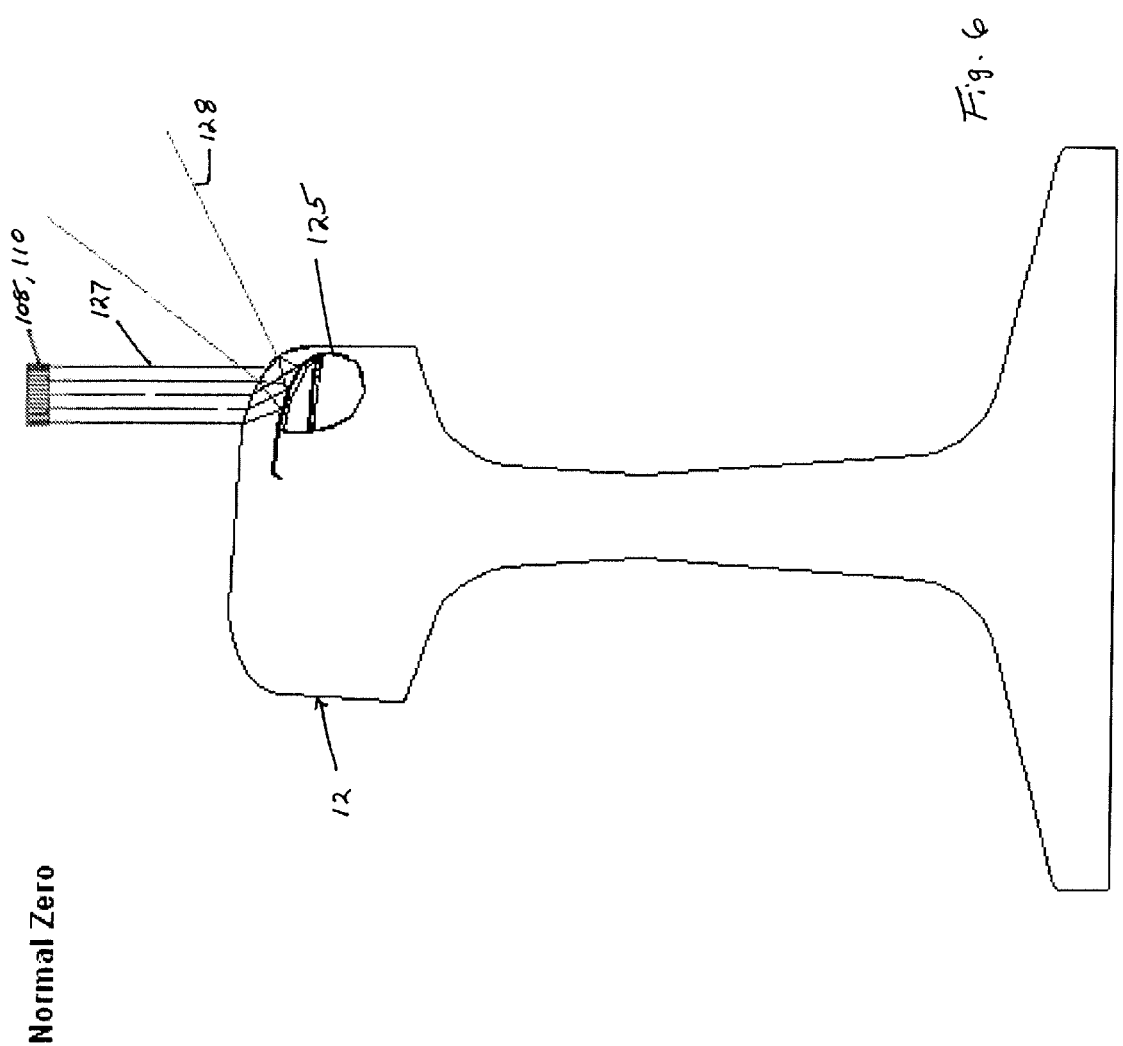

Referring now to FIG. 6 there is shown a railroad rail with an internal defect 125 in the head 12 of the rail. Defect 125 is essentially parallel to the surface of the rail head and is a schematic representation of the type of defect shown in FIGS. 2-5. As set forth above, this type of defect was heretofore extremely difficult to detect or undetectable with known prior art technology.

As shown in FIG. 6, if an attempt is made to detect defect 125 with a zero degree probe, such as probes 108 or 110, the reflection echo 128 from ultrasonic beam 127 will not be returned to transducers 108 or 110 and thus the defect will not be detected. The end view in FIG. 6 shows a zero transducer when not tilted from the vertical. The position of the transducers when not tilted 8-14 degrees from the vertical is analogous to the position of the leading and the trailing wheels on the rail as shown in FIGS. 2 and 3 of U.S. Pat. No. 4,165,648, which is incorporated by reference, and is shown here by FIGS. 6 and 8A.

The teaching of the present invention with respect to the third single (or sensing) wheel 21 on the rail 12 is shown using end schematic section views of FIGS. 7, 9A, 9B, and 10A, 10B. Here, when looking at the end view of the rail 12, the third single wheel 21 is shown angled to the left or right of the rail or, stated a different way, the wheel 21 is tilted perpendicular to the vertical plane and out of vertical alignment with the rail 12.

Figure 7:
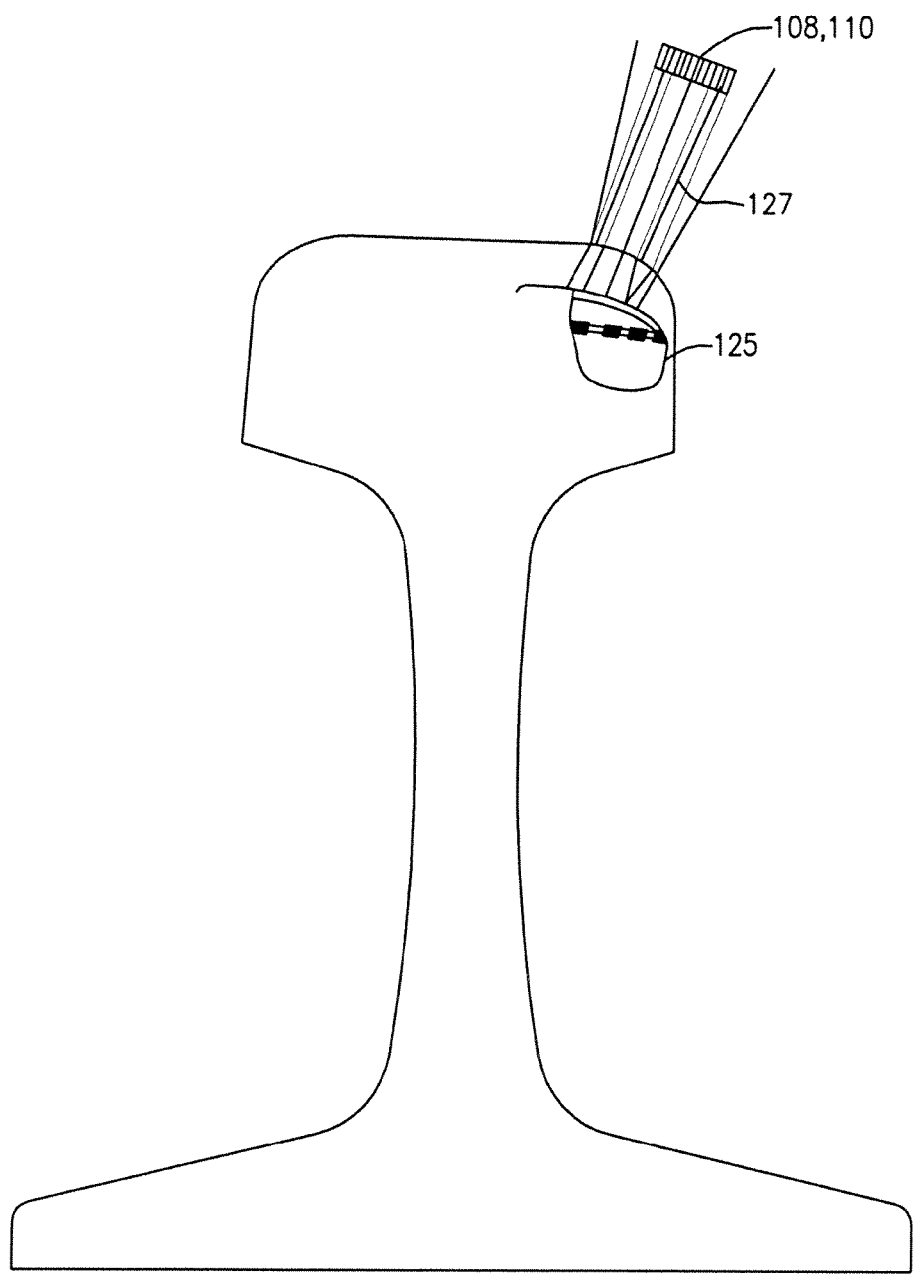

Referring now to FIG. 7 there is shown that same defect 125, described above. However, in this instance the zero degree transducer 1100 of third single or sensing wheel 21 is tilted 8-14 degrees from the vertical by tilting of the wheel 21. With this change ultrasonic beam 127 is returned perpendicular to the horizontal component of the detail fracture and detected by transducers 1100.

FIGS. 8A and 8B show the use of the 70 degree transducer without being tilted, with FIG. 8A being an end view of the rail and FIG. 8B being a side view. As shown, if the 70 degree transducer is not tilted the return ultrasonic beam is directed away from transducer 118 and detail fracture 125 will not be detected.

Figure 9B:
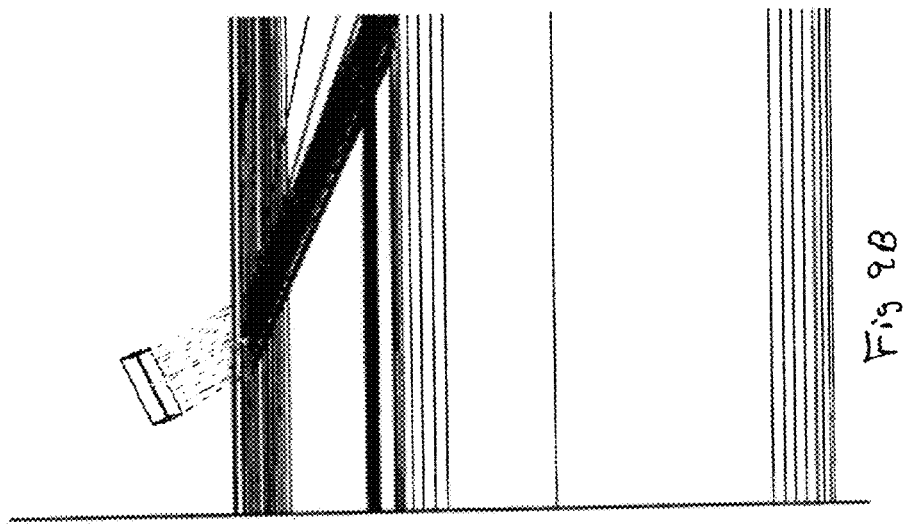
Figure 9A:
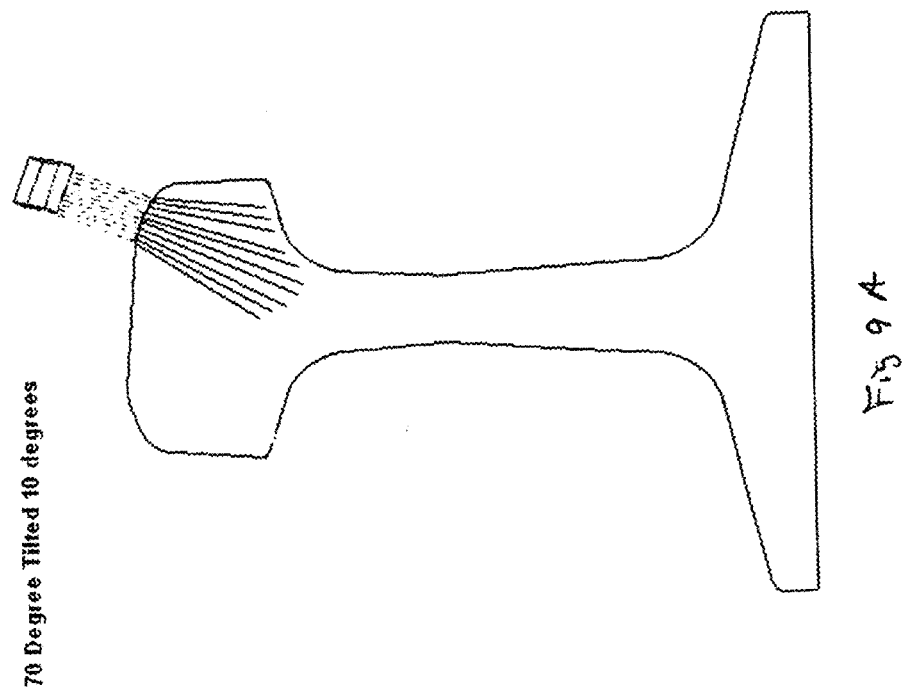

FIGS. 9A and 9B show an end and side view respectively with the 70 degree transducer 1120, 1180 of third single or sensing wheel 21 tilted 10 degrees. As shown the ultrasonic beam penetrates directly into the rail head and propagates down the rail making the ultrasonic return essentially immune to rail surface conditions which can cause detection error.

Figure 10B:
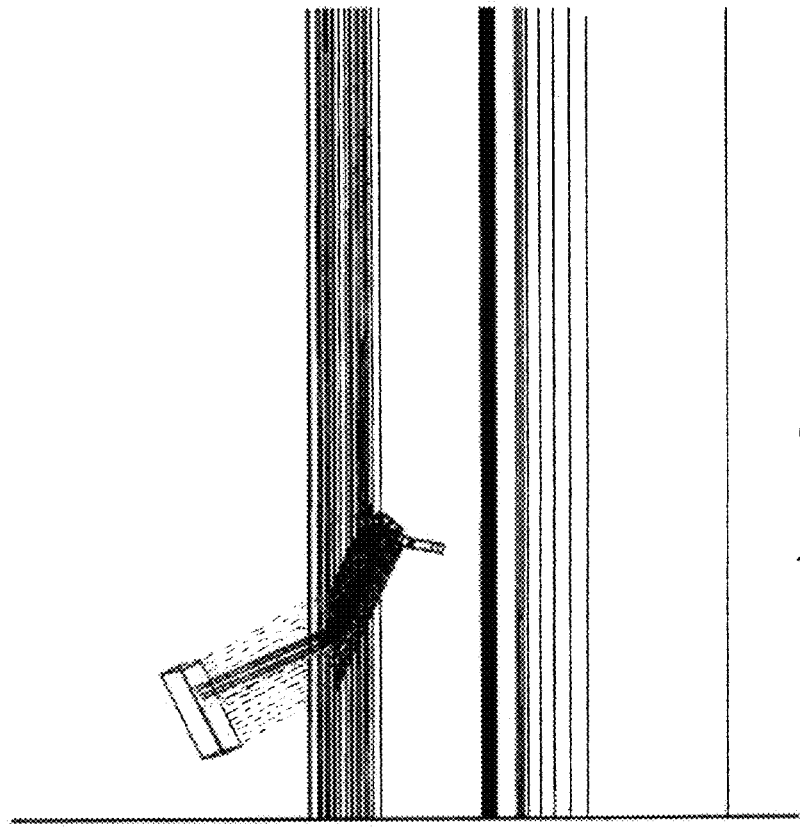
Figure 10A:
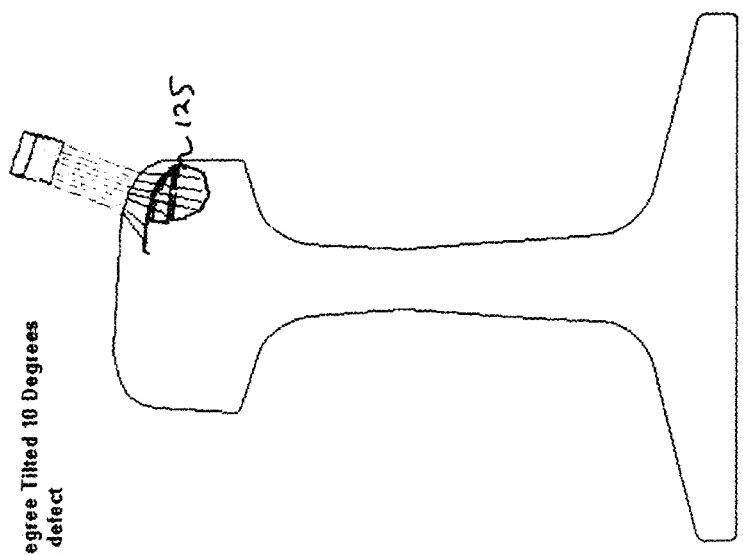

FIGS. 10A and 10B show an end and side view respectively with the 70 degree transducer 1120, 1180 of third single or sensing wheel 21 tilted 10 degrees and also showing detail fracture 125. With the 10 degree tilt the ultrasonic beam is reflected back towards the transducer so that detail fracture 125 is detected.

Tilting the zero degree 1100 and 70 degree transducers 1120, 1180 of third single or sensing wheel 21 8-14 degrees from the vertical can be readily accomplished by tilting the single sensing wheel used with the present invention or alternatively tilting the actual transducers. The sensing wheels used in U.S. Pat. No. 4,165,648 did not and could not tilt but various mechanical arrangements are possible in order to tilt the test wheels or the transducers, all of which would be apparent to one skilled in this art area.

The present invention provides an apparatus for performing ultrasonic inspection of a length of test material, such as a railroad rail, with ultrasonic transducing means emitting a beam of ultrasonic energy from within sealed wheel means and arranged for rolling contact along the test material. The apparatus includes a sensing wheel arranged for rolling contact along the length of the rail and an ultrasonic transducer included in the sensing wheel. The ultrasonic transducer is aimed downwardly approximately between 8° and 14° from the perpendicular to the top surface of the rail and aimed toward a lower gauge corner of the rail whereby said ultrasonic transducer effectively probes the lower gauge corner of the rail for internal rail defects having a horizontal component and a transverse component. See for example FIGS. 2 and 3 in U.S. Pat. No. 4,165,648.

The present invention provides a system for performing ultrasonic inspection of a rail comprising using a third sensing wheel 21 in conjunction with a leading wheel 20 and a trailing wheel 22. The leading 20 and trailing wheels 22 are aligned in a vertical plane with the rail and include 0 degree transducer 108, 110 that emits ultrasound beams into the rail at zero degree, and 70 degree transducers being oriented at an angle from said first transducer to emit ultrasound beams into the rail at 70 degrees in accordance with the teachings in U.S. Pat. No. 4,165,648 which is incorporated by reference. The position of each the 0 degree transducer and 70 degree transducers within each the leading wheel and trailing wheel are said to be a standard position.

The third sensing wheel 21 is arranged to roll along an upper surface of the rail behind the leading wheel and a trailing wheel and is tilted between 8° and 14° in a direction perpendicular to the vertical plane by arm 23, said third sensing wheel includes a first sensing wheel transducer and at least one second sensing wheel transducer that are equivalent in position within the third sensing wheel to the 0 degree transducer and the 70 degree transducer that are within the leading and trailing wheels, respectively. The first sensing wheel transducer emits ultrasonic beams into the rail to detect horizontal defects in the rail and said second sensing wheel transducer emits ultrasonic beams into the rail to detect transverse defects in the rail that are normally undetectable when probed by ultrasonic beams directed perpendicular to the surface of the rail.

It is to be understood that a rotation of 8° to 14° is an example of a working embodiment which could vary. What is required for implementation of the inventive concept described herein is sufficient rotation such that the ultrasonic beam is deflected from the target defect in such a way that the return echo is detected by the transducers.

Although a specific embodiment of the invention has been disclosed herein it is to be understood that various modifications can be made to the described embodiment without departing from the scope of the claimed invention, which modification, would be apparent to one skilled in this art area.

The invention claimed is:

1. A system for performing ultrasonic inspection of a rail comprising:
    a sensing wheel arranged to roll along the top of the rail;
    ultrasonic transducers in said sensing wheel, each ultrasonic transducer able to direct an ultrasonic beam into the rail; and
    said sensing wheel being tilted perpendicular to the vertical plane extending from the rail, and thus out of vertical alignment with the rail, the amount of tilt from the vertical plane being sufficient to detect defects in the rail which result from longitudinal cracks that propagate in the horizontal and transverse plane of the rail and are normally undetectable when probed by ultrasonic beams directed perpendicular to the surface of the rail.

2. A system in accordance with claim 1 wherein said sensing wheel is tilted between 8° and 14° from the vertical plane.

3. A system in accordance with claim 1 wherein said sensing wheel is disposed behind a leading wheel and a trailing wheel and said sensing wheel is tilted by an arm attached to said sensing wheel.

4. A system in accordance with claim 1 wherein said tilted sensing wheel includes a first sensing wheel transducer and at least one second sensing wheel transducer, said first sensing wheel transducer emits ultrasonic beams into the rail to detect horizontal defects in the rail and said second sensing wheel transducer emits ultrasonic beams into the rail to detect transverse defects in the rail that are normally undetectable when probed by ultrasonic beams directed perpendicular to the surface of the rail.

5. A system for performing ultrasonic inspection of a rail comprising:
    at least one sensing wheel arranged to roll along the top of the rail;
    ultrasonic transducers in each said sensing wheel, each ultrasonic transducer able to direct an ultrasonic beam into the rail; and
    each said sensing wheel being tilted out of vertical alignment with the rail and between 8° and 14° from a vertical plane extending perpendicular to the rail, the amount of tilt from the perpendicular being sufficient to detect defects in the rail which result from longitudinal cracks that propagate in the horizontal and transverse plane of the rail and are normally undetectable when probed by ultrasonic beams directed perpendicular to the surface of the rail.

6. A system for performing ultrasonic inspection of a rail comprising:
- a leading wheel and a trailing wheel, said leading and said trailing wheels being aligned in a vertical plane with said rail, said leading and trailing wheels each include a first transducer and at least one second transducer, said first transducer being oriented in said leading and said trailing wheel to emit ultrasound beams into the rail at zero degree, and said second transducer being oriented at an angle from said first transducer to emit ultrasound beams into the rail at 70 degrees, each said first and said second transducers within each said leading and said trailing wheel being oriented in a standard position; and
- a third sensing wheel arranged to roll along an upper surface of the rail, said third sensing wheel being tilted out of vertical alignment with the rail in a direction perpendicular to said vertical plane by an arm, said third sensing wheel includes a first sensing wheel transducer and at least one second sensing wheel transducer, said first sensing wheel transducer and said second sensing wheel transducer being oriented within the tilted third sensing wheel in said standard position wherein said first sensing wheel transducer emits ultrasonic beams into the rail to detect horizontal defects in the rail and said second sensing wheel transducer emits ultrasonic beams into the rail to detect transverse defects in the rail that are normally undetectable when probed by ultrasonic beams directed in a vertical alignment with the rail.

7. A system in accordance with claim 6 wherein said sensing wheel is disposed between said leading wheel and said trailing wheel.

8. A system in accordance with claim 6 wherein said arm tilts the sensing wheel between 8° and 14° from the vertical plane.

* * * * *